United States Patent [19]

Hopp et al.

[11] Patent Number: 5,189,230

[45] Date of Patent: Feb. 23, 1993

[54] PROCESS FOR THE REMOVAL OF OLEFINIC IMPURITIES FROM HYDROCHLOROFLUOROCARBONS

[75] Inventors: Peter Hopp, Hofheim am Taunus; Rolf-Michael Jansen, Kelkheim, both of Fed. Rep. of Germany

[73] Assignee: Hoechst Aktiengesellschaft, Frankfurt am Main, Fed. Rep. of Germany

[21] Appl. No.: 806,494

[22] Filed: Dec. 13, 1991

[30] Foreign Application Priority Data

Dec. 21, 1990 [DE] Fed. Rep. of Germany ....... 4041181

[51] Int. Cl.$^5$ .............................................. C07C 17/38
[52] U.S. Cl. .................................................... 570/177
[58] Field of Search ................................. 570/177, 178

[56] References Cited

U.S. PATENT DOCUMENTS 3,696,156 10/1972 Weeks .................................. 260/648

FOREIGN PATENT DOCUMENTS 0370688 5/1990 European Pat. Off. .
1219460 6/1966 Fed. Rep. of Germany ...... 570/178
1401541 7/1975 United Kingdom .

OTHER PUBLICATIONS

Anderson, A. L. et al., *J. Fluorine Chem.* 1, 121-122 (1971).

*Primary Examiner*—Alan Siegel
*Attorney, Agent, or Firm*—Connolly and Hutz

[57] ABSTRACT

The invention relates to a process for the removal of olefins of the formula $C_nH_xF_yA_z$, in which A is chlorine and/or bromine and n is a number from 2 to 4, x and y are each a number from 1 to 6 and z is a number from 1 to 4, the sum of $x+y+z$ being equal to 2n, from hydrochlorofluorocarbons of the formula $C_2H_mF_pA_q$, in which A is chlorine and/or bromine and m and p are each a number from 1 to 5 and q is a number from 0 to 4, the sum of $m+p+q$ being equal to 6, which comprises reacting the hydrochlorofluorocarbons $C_2H_mF_pA_q$ which are contaminated with the olefins mentioned, in the presence of oxygen-containing phase-transfer catalysts with complex hydrides and/or strong bases.

14 Claims, No Drawings

PROCESS FOR THE REMOVAL OF OLEFINIC IMPURITIES FROM HYDROCHLOROFLUOROCARBONS

DESCRIPTION

Process for the removal of olefinic impurities from hydrochlorofluorocarbons

The present invention relates to a process for the removal of olefinic impurities from hydrochlorofluorocarbons (HCFCs)

HCFCs of the formula $C_2H_mF_pA_q$, in which A is chlorine and/or bromine and m and p are each the numbers 1 to 5 and q the numbers 0 to 4, the sum of $m+p+q$ being equal to 6, in particular the compounds 1,1-dichloro-2,2,2-trifluoroethane $CF_3CHCl_2$ (R 123) and 1,1,1,2-tetrafluoroethane $CF_3CH_2F$ (R 134a), are of particular industrial interest as environmentally harmless substitutes for chlorofluorocarbons, which are suspected of destroying the upper ozone layer of the earth's atmosphere. During synthesis of these HCFCs, toxic olefinic impurities of the formula $C_nH_xF_yA_z$, in which A is chlorine and/or bromine and n is the numbers 2 to 4, x and y are each the numbers 1 to 6 and z the numbers 1 to 4, the sum of $x+y+z$ being equal to $2n$, are often formed as byproducts, in particular 1,1,1,4,4,4-hexafluoro-2-chloro-2-butene (R 1326) or 1,1-difluorochloroethene (R 1122), which have to be separated off chemically or physically, in order to enable the HCFCs to be used without any risk for the environment as foaming agents or in refrigeration engineering.

According to the prior art, olefins from CFC mixtures can be converted into other products by gas phase reaction with metal oxides (EP-A1 370,688 and U.S. Pat. No. 3,696,156) or by photochlorination (GB-A 1,401,541). Furthermore, it is known that fluorinated ethylenes can be hydrogenated with sodium borohydride in diglyme in the presence of added water, ethanol or tertiary butanol at 0° to 5° C. (J. Fluorine Chem. 1 (1971), 121).

However, the processes mentioned for the removal of olefins from CFCs are not suitable for removing the olefinic impurities completely from the HCFCs. When the HCFCs mentioned are purified by distillation, residues of olefinic impurities remain in the distillate. The process described in the last-mentioned publication for the hydrogenation of fluorinated ethylenes with sodium borohydride is exclusively carried out in a protic, i.e. in an aqueous or alcoholic, medium and at a maximum temperature of 5° C. However, this process is not very suitable for solving the problem at hand, since the use of aqueous solvents would subsequently require an additional drying step. Alcohols cannot therefore be considered as solvents, since they form azeotropes with many CFCs and HCFCs.

The object of the present invention is to provide a process which removes olefinic impurities, in particular the compounds R 1326 and R 1122 already mentioned, completely from HCFCs and converts them into non-toxic products without attacking the HCFCs.

The invention relates to a process for the removal of olefins of the formula $C_nH_xF_yA_z$, in which A is chlorine and/or bromine and n is a number from 2 to 4, x and y are each a number from 1 to 6 and z is a number from 1 to 4, the sum of $x+y+z$ being equal to $2n$, from hydrochlorofluorocarbons of the formula $C_2H_mF_pA_q$, in which A is chlorine and/or bromine and m and p are each a number from 1 to 5 and q is a number from 0 to 4, the sum of $m+p+q$ being equal to 6, which comprises reacting the hydrochlorofluorocarbons $C_2H_mF_pA_q$ which are contaminated with the olefins mentioned, in the presence of oxygen-containing phase-transfer catalysts with complex hydrides and/or strong bases. The reaction is carried out in the absence of protic media. Preferred oxygen-containing phase-transfer catalysts are crown ethers or polyethylene glycol dialkyl ethers of the formula $RO(CH_2CH_2O)_aR'$, in which R and R', independently of one another, are methyl, ethyl, n-propyl, iso-propyl, n-butyl, sec-butyl, iso-butyl or tert-butyl and a is a number from 2 to 10.

Of the polyethylene glycol dialkyl ethers mentioned, those in which R and R', independently of one another, are methyl or ethyl are preferred.

Preferred crown ethers are benzo-12-crown-4, benzo-15-crown-5, 12-crown-4, 15-crown-5, dibenzo-18-crown-6, dibenzo-24-crown-8, dicyclohexyl-18-crown-6, dicyclohexyl-24-crown-8, 4'-nitrobenzo-15-crown-5 or N,N-dibenzyl-4,13-diaza-18-crown-6.

Preferred crown ethers are 18-crown-6, dibenzo-18-crown-6 and dicyclohexyl-18-crown-6, in particular 18-crown-6.

Complex hydrides which can be used for the process according to the invention are lithium aluminum hydride, lithium borohydride, lithium 9-borobicyclononane hydride, lithium tert-butyl diisobutylaluminum hydride, lithium dimethylborohydride, lithium tert-hexylborohydride, lithium tert-butoxyaluminum hydride, lithium tri(sec-butyl)borohydride (L-Selectide ®), lithium triethylborohydride, sodium borohydride, sodium cyanoborohydride, sodium triacetoxyborohydride, sodium triethylborohydride, sodium trimethoxyborohydride and sodium tri(sec-butyl)borohydride.

Preferred complex hydrides are sodium borohydride, sodium cyanoborohydride and lithium aluminum hydride, in particular sodium borohydride.

Preferred strong bases are alkali metal hydrides, alkali metal alcoholates and alkali metal hydroxides, in particular sodium hydride, lithium hydride, sodium methoxide, potassium tert-butoxide, sodium hydroxide and potassium hydroxide.

The oxygen-containing phase-transfer catalyst is used in an amount of 1 to 20% by weight, relative to the HCFC used.

The strong base and/or the complex hydride are/is used in an amount of 0.5 to 10% by weight, relative to the HCFC used. It is possible to use a complex hydride together with a hydride as the strong base but not together with an alcoholate or a hydroxide as the strong base. Furthermore, a mixture of several alcoholates and/or hydroxides can be used as the strong base but not together with a hydride as the strong base.

After the reaction, the HCFCs can be obtained in pure form by fractional distillation, which is not possible without the reaction according to the invention of the olefinic impurities. The process is suitable in particular for purifying the HCFCs 1,1-dichloro-2,2,2-trifluoroethane and 1,1,1,2-tetrafluoroethane, in which 1,1,1,4,4,4-hexafluoro-2-chloro-2-butene and/or 1,1-difluorochloroethene are present as olefinic impurities.

The process according to the invention is in general carried out at temperatures from 0° to 150° C. and atmospheric pressure (1 bar) or in an autoclave at pressures from 1 to 80 bar, preferably 15 to 40 bar, and at temperatures from 0° to 150° C., preferably from 50° to 100° C.

The process is illustrated in more detail by means of the examples below.

The HCFC 1,1-dichloro-2,2,2-trifluoroethane (R 123) used in the examples contained 1500 ppm of 1,1,1,4,4,4-hexafluoro-2-chloro-2-butene (R 1326), and the HCFC 1,1,1,2-tetrafluoroethane (R 134a) contained 2000 ppm of 1,1-difluorochloroethene (R 1122) as olefinic impurities. The R 1326 and R 1122 contents were in each case determined by gas chromatography.

EXAMPLE 1

10 ml of R 123 were stirred together with 0.5 g of $NaBH_4$ in 0.5–1.0 ml of 18-crown-6 at 20° C. The R 1326 content determined after 12 hours was 0 ppm.

In the examples below, the procedure was analogous and the complex hydride or the strong base and the phase-transfer catalyst (PTC) were varied.

| Example | Complex hydride or base | PTC | R 1326 content in ppm after 12 hours |
|---|---|---|---|
| 2 | $NaBH_4$ | diethylene glycol dimethyl ether | 0 |
| 3 | $NaBH_4$ | polyethylene glycol dimethyl ether | 0 |
| 4 | LiH | 18-crown-6 | 1280 |
| 5 | NaH | 18-crown-6 | 0 |
| 6 | NaOMe | 18-crown-6 | 230 |
| 7 | KO$^t$Bu | 18-crown-6 | 0 |
| 8 | NaOH | 18-crown-6 | 0 |
| 9 | KOH | 18-crown-6 | 0 |

EXAMPLE 10

26 g of R 134a were reacted together with 2 g of $NaBH_4$ and 4 ml of diethylene glycol dimethyl ether in an autoclave at a temperature of 110° C. and a pressure of 5.2 bar. The R 1122 content determined after 12 hours was 0 ppm. In the examples below, the procedure was analogous and $NaBH_4$ was replaced by a strong base:

| Example | Strong base | R 1122 content in ppm after 12 hours |
|---|---|---|
| 11 | NaH | 0 |
| 12 | KO$^t$Bu | 0 |
| 13 | NaOH | 0 |

We claim:

1. A process for the removal of olefins of the formula $C_nH_xF_yA_z$, in which A is chlorine and/or bromine and n is a number from 2 to 4, x and y are each a number from 1 to 6 and z is a number from 1 to 4, the sum of x+y+z being equal to 2n, from hydrochlorofluorocarbons of the formula $C_2H_mF_pA_q$, in which A is chlorine and/or bromine and m and p are each a number from 1 to 5 and q is a number from 0 to 4, the sum of m+p+q being equal to 6, which comprises reacting the hydrochlorofluorocarbons $C_2H_mF_pA_q$ which are contaminated with the olefins mentioned, in the presence of oxygen-containing phase-transfer catalysts with complex hydrides and/or strong bases wherein said process is carried out in the absence of protic media.

2. The process as claimed in claim wherein the hydrochlorofluorocarbons are compounds having the empirical formulae $C_2H_2F_3Cl$, $C_2HF_3Cl_2$ or $C_2H_2F_4$.

3. The process as claimed in claim 1, wherein the hydrochlorofluorocarbons are 1,1-dichloro-2,2,2-trifluoroethane or 1,1,1,2-tetrafluoroethane.

4. The process as claimed in claim 1, wherein the olefins are compounds of the formulae $C_2HF_2Cl$ or $C_4HF_6Cl$.

5. The process as claimed in claim 1, wherein the oxygen-containing phase-transfer catalyst is a crown ether.

6. The process as claimed in claim 1, wherein the oxygen-containing phase-transfer catalyst is one of the crown ethers 18-crown-6, dibenzo-18-crown-6 or dicyclohexyl-18-crown-6.

7. The process as claimed in claim 1, wherein the oxygen-containing phase-transfer catalyst is a polyethylene glycol dialkyl ether of the formula $RO(CH_2CH_2O)_aR'$, in which R and R', independently of one another, are methyl, ethyl, n-propyl, iso-propyl, n-butyl, sec-butyl, iso-butyl or tert-butyl and a is a number from 2 to 10.

8. The process as claimed in claim 1, wherein the oxygen-containing phase-transfer catalyst is a polyethylene glycol dialkyl ether of the formula $RO(CH_2CH_2O)_aR'$, in which R and R', independently of one another, are methyl or ethyl and a is a number from 2 to 10.

9. The process as claimed in claim 1, wherein the strong base is an alkali metal alcoholate and/or an alkali metal hydroxide.

10. The process as claimed in claim 1, wherein the strong base is sodium methoxide, potassium tert-butoxide, sodium hydroxide and/or potassium hydroxide.

11. The process as claimed in claim 1, wherein the strong base is an alkali metal hydride.

12. The process as claimed in claim 1, wherein the strong base is lithium hydride and/or sodium hydride.

13. The process as claimed in claim 1, wherein the complex hydride is sodium borohydride, sodium cyanoborohydride or lithium aluminum hydride.

14. The process as claimed in claim 1, wherein the complex hydride is sodium borohydride.

* * * * *